United States Patent [19]

Gardner, Jr.

[11] Patent Number: 5,203,352
[45] Date of Patent: Apr. 20, 1993

[54] POLYMERIC FOAM EARPLUG

[75] Inventor: Ross Gardner, Jr., Indianapolis, Ind.

[73] Assignee: Cabot Safety Corporation, Southbridge, Mass.

[21] Appl. No.: 598,268

[22] Filed: Oct. 16, 1990

[51] Int. Cl.⁵ .............................................. A61F 11/00
[52] U.S. Cl. ..................................... 128/864; 604/369
[58] Field of Search ............... 128/864, 865, 866, 867, 128/868; 604/369, 370

[56] References Cited

U.S. PATENT DOCUMENTS

| | | | |
|---|---|---|---|
| Re. 29,487 | 12/1987 | Gardner | 128/152 |
| 2,262,568 | 11/1941 | Wade | 128/152 |
| 3,736,929 | 6/1973 | Mills | 128/864 |
| 4,158,087 | 6/1979 | Wood | 521/137 |
| 4,193,396 | 3/1980 | Wacker | 128/864 |
| 4,293,355 | 10/1981 | Wacker | 128/864 |
| 4,579,112 | 4/1986 | Scott | 128/864 |
| 4,774,938 | 10/1988 | Leight | 128/864 |

FOREIGN PATENT DOCUMENTS 0108728  5/1988  European Pat. Off. .
6907047  10/1969  Netherlands .

*Primary Examiner*—Robert A. Hafer
*Assistant Examiner*—David J. Kenealy
*Attorney, Agent, or Firm*—Michelle B. Lando; Harry J. Gwinnell

[57] ABSTRACT

Disclosed herein are hearing protective earplug constructions of the roll-down type. In one aspect the constructions employ means to limit the depth of insertion of the earplug into the ear canal and to facilitate proper insertion thereof. In another aspect, the constructions employ polymeric foam bodies adapted to be compressed, inserted into the ear canal and there allowed to expand to obturate the ear canal and whose recovery time is markedly and inversely temperature dependent.

23 Claims, 4 Drawing Sheets

POLYMERIC FOAM EARPLUG

BACKGROUND OF THE INVENTION

1. Field of the Invention

The present invention relates generally to hearing protective earplugs and is more particularly concerned with polymeric foam earplugs of the roll-down type.

2. Background of the Prior Art

In my prior U.S. Pat. No. Re. 29,487 there is taught a roll-down type hearing protective earplug composed of a slow recovery viscoelastic polymeric foam and having a size and shape adapted to be compressed, inserted into the human ear canal and therein allowed to expand to result in an acoustic obturation of the ear canal. Earplugs manufactured in accordance with the aforementioned patent have met with outstanding commercial success in the marketplace due to their features of easy insertability, comfort, excellent attenuation properties and their ability to be produced in a single size while competently fitting almost the entire adult population. Such an earplug is utilized by first rolling it down between thumb and fingers to the extent that it is compressed in cross section to below the size of the ear canal into which it is to be inserted. In accordance with the instructions, the thusly compressed earplug is then inserted into the ear canal and held at the inserted depth with a fingertip for enough time as to allow the polymeric foam to recover sufficiently to seat the plug within the ear canal. Unfortunately, some users ignore or forget the instructions and tend either to not insert the compressed plug into the ear canal to an adequate depth and/or to release the inserted plug prematurely. Of course, when the plug is released before such time as it seats itself within the ear canal it can slip to a lesser or greater depth of insertion. This can lead to inadequate acoustic sealing of the ear canal or to difficulty in removal of the plug. In accordance with the present invention, however, these problems have been substantially completely overcome.

In published European Application 108 728, Chiavacci et al., filed Nov. 3, 1983, "Fascicule" published May 4, 1988, there is disclosed a polymeric foam earplug having a first section for insertion into the ear canal and, coaxially affixed thereto, a second section. The first and second sections are each composed of a polymeric foam material. However, the polymeric foam material of the second section, which is expressly defined as constituting a hand-grip for the introduction of the first section into the ear canal, is composed of a harder, more dense material than the foam material of the first section. Mechanical fixation of the first section to the second section is by surface interpenetration of the respective foam materials along their common boundary. With respect to the present invention, it is noteworthy that the criteria attendant of the foam materials of the first and second sections of the earplug disclosed in EP 108 728 are density and hardness and that, contrary to the present invention, no significance attaches to the recovery times thereof.

Published Dutch Patent Application No. 6907047, to Klosterfrau Berlin, published Nov. 11, 1969, discloses an earplug of the push-in type comprising a soft elastic polymer foam "frame" or "carrier" which has been impregnated with a non-elastic, deformable and heat softenable plastic material. The non-elastic heat softenable plastic material impregnant can be any one of a number of wax compositions and serves to stiffen the earplug structure sufficiently at room temperature so as to facilitate the push-in mode of insertion of the plug into the ear canal. Subsequent to insertion, the body heat of the ear canal causes softening of the non-elastic plastic material impregnant, thereby allowing the elastic polymeric foam "frame" or "carrier", which is partially compressed by the ear canal wall acting as a die during the push-in insertion thereof into the ear canal, to expand and to occlude the ear canal. By virtue of the impregnation of the elastic polymeric foam "frame" material with the non-elastic heat softenable plastic material, the Klosterfrau Berlin earplug construction is essentially a hydraulic system whereby deformation of the plug by compression thereof does not result in a corresponding decrease in the volume of the plug. Rather, when such a plug is compressed in one plane, by reason of its hydraulic nature it inherently expands in at least one of the planes normal to the plane of compression thereof. Thus, when squeezed lengthwise in free space in one plane, the Klosterfrau Berlin plug expands in the plane rotated 90° to the plane of compression. When subject to the compressive forces brought to bear thereon by push-in insertion and extrusion into the ear canal, the Klosterfrau Berlin plug tends to respond by increasing its length and not by a reduction in the overall volume thereof.

Another polymeric foam earplug construction dependent upon impregnation of the foam structure thereof with a wax in order to stiffen the structure sufficiently to enable push-in type insertion into the ear canal is disclosed in U.S. Pat. No. 2,262,568, to Wade, Nov. 11, 1941. Wade discloses a hearing protector composed of a body of porous latex foam, one end of said body being designated for insertion into the ear canal and being impregnated with an amorphous wax/petroleum jelly mixture having a melting point of about 125° F. (or at least above body temperature) and the other end of said body being designated to reside outside the ear canal and to be utilized as a means for holding the device for insertion and removal and being free of such wax impregnation. According to Wade, his earplug construction requires no kneading or adjustment prior to insertion. In addition, Wade discloses that the wax impregnated section of his earplug device is inelastic in nature.

It should be noted that, unlike the roll-down earplug construction of the present invention, each of the wax-impregnated devices of Klosterfrau Berlin and Wade is designed as a push-in type earplug and both are absolutely dependent upon wax impregnation of an elastic polymeric foam body as the key modality by which to stiffen the device sufficiently to allow this push-in mode of insertion to be achieved. Additionally, as mentioned above, the wax filled cellular structures of the Klosterfrau Berlin and Wade push-in type earplugs react to compression deformation thereof in the manner of hydraulic systems. Contrarily, the roll-down type earplug construction contemplated by the present invention is composed of polymeric foam materials whose cellular structures are gas-filled, thereby to avoid the hydraulic system responses to compression outlined above.

OBJECTS OF THE INVENTION

It is a principal object of the invention to provide a new and novel polymeric foam earplug construction.

It is another object of the invention to provide a polymeric foam earplug construction of the roll-down type comprising stop means to automatically control the depth of insertion thereof into the ear canal.

It is still another object of the invention to provide a polymeric foam earplug construction of the roll-down type comprising means to automatically stabilize the earplug in the ear canal of the wearer substantially immediately after its insertion and during its recovery to form an acoustic seal of the ear canal.

It is yet another object of the invention to provide a polymeric foam earplug construction having improved attenuation properties in the low frequency range.

Other objects and advantages of the present invention will in part be obvious and will in part appear hereinafter.

SUMMARY OF THE INVENTION

In accordance with the invention, the earplug construction hereof comprises a resilient polymeric foam body whose cellular volume is gas filled, the body having a nose section and a tail section. The nose section is composed of a slow recovery, viscoelastic, polymeric foam and is of a size and shape adapted to be compressed or rolled down and inserted into the human ear canal and there allowed to expand and obturate the ear canal. The essentials of the nose section are similar to those of the earplug disclosed and claimed in my prior U.S. Pat. No. Re. 29,487; namely, a room temperature recovery time from 60 percent compression to 40 percent compression thereof of at least 1 second and an equilibrium pressure at 40 percent compression thereof of from 0.2 to 1.3 p.s.i. The resilient polymeric foam tail section of the present construction, which is coextensive with the nose section, remains outside the ear canal during use and is of considerably more elastic nature than the nose section. The relatively elastic tail section has a recovery time from 60 percent compression to 40 percent compression which is no greater than about 50% of the recovery time of the nose section and in no event exceeds 5 seconds. In a preferred embodiment of the invention the nose section is composed of a viscoelastic foam composition which exhibits inversely temperature dependent recovery time properties, the recovery time of the nose section at room temperature (21°-23° C.) from 60 percent compression to 40 percent compression thereof being greater than 60 seconds and the recovery time of the nose section at body temperature (35.6° C.) being less than (e.g., one-third or less) the recovery time at room temperature, and in no event, in excess of 90 seconds.

DESCRIPTION OF THE PREFERRED EMBODIMENTS

Figure 1:
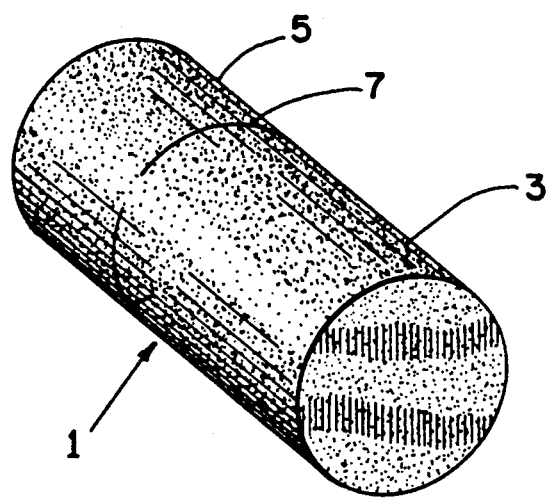
FIG. 1 hereof is a perspective view of an earplug in accordance with the invention and being producible by die cutting of a two-layer sheet foam composite.
Figure 2:
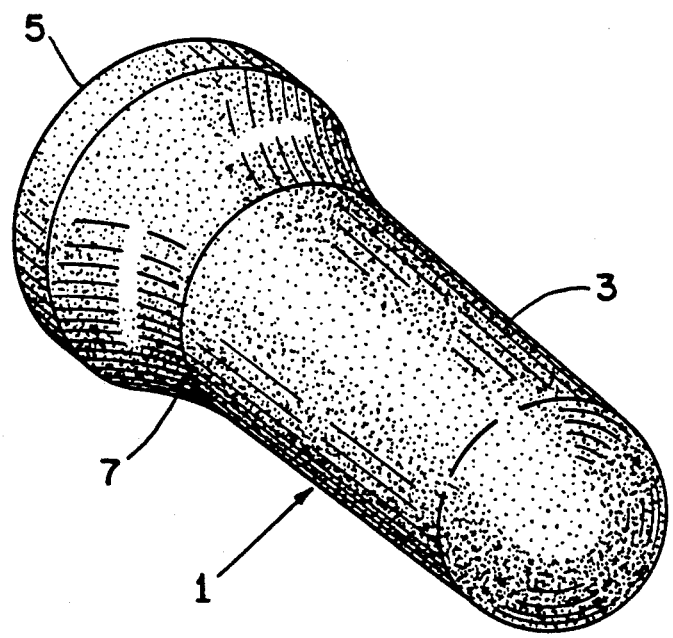
FIG. 2 is a perspective view of another embodiment of an earplug in accordance with the invention and which is producible by molding of two polymeric foam precursor compositions deposited serially into a suitable mold.

Referring now to FIGS. 1 and 2, wherein like reference numerals refer to like structures, the polymeric foam earplug construction of the invention broadly comprises a resilient polymeric foam body 1 having a slow recovery viscoelastic nose section 3 and, coextensive therewith, a relatively substantially faster recovery, more elastic, tail section 5. Fixation of the nose section 3 to the tail section 5 can be achieved in any suitable manner, such as by means of a suitable adhesive, solvent welding or thermal welding of the respective sections. In general, however, it is preferred that said fixation be achieved by direct bonding of the two polymeric foam sections together either by molding of two serially deposited polymeric foam purchaser compositions in a mold or by manufacture of a two-layer sheet of the earplug foam materials followed by die cutting of earplugs therefrom. By directly bonding the sections 3 and 5 together, in other words, by avoiding the interposition of glues, adhesives, thermoplastic sheets and the like between said sections, there is generally avoided a parting line 7 which feels distinctly different from the polymeric foam sections themselves and this avoidance is desirable from the standpoint of maximizing the sensed comfort of the plug during its use. The molding technique outlined above inherently results in such direct bonding of the nose section 3 to the tail section 5. Suitable techniques by which to achieve such direct bonding of the nose section 3 foam material to the tail section 3 foam material in the preparation of two-layer composite foam sheets for die cutting purposes will appear hereinafter.

There are many resilient polymeric foam compositions which may be formulated by those of skill in the art to meet the viscoelastic and relatively elastic recovery property requirements for the nose and tail sections 3 and 5 of the invention. For instance, many of the externally and internally plasticized polymeric foams disclosed in my U.S. Pat. No. Re. 29,487 are generally suitable for use as a material of construction of the viscoelastic nose section 3. By suitable selections of plasticizers, blowing agents, ingredient concentrations and blowing regimens, all of which is within the skill of the art, similar foam formulations having the physical property requirements of the tail section 5 can be achieved. Similarly, many of the polyurethane foam formulations lying within the ambit of U.S. Pat. No. 4,158,087, to Louis Leonard Wood, Jun. 12, 1979, entitled, "Urethane Foams Having Low Resiliency", are possessed of the necessary viscoelastic properties for use as the nose section 3 of the invention. By suitable adjustment of the ingredients in such formulations similar formulations suitable for use as the tail section 5 of the invention can readily be prepared. The disclosure of each of the foregoing patents is incorporated herein, in its entirety, by reference.

Polyurethane foam compositions are generally preferred as the materials for the nose and tail sections 3 and 5 due to their formulation flexibility, easy processing characteristics and economics. Of these, polyether polyurethane foams are even further preferred due to the generally soft surface "hand" or feel of resilient foam wares produced therewith. The polyether polyurethane foam compositions based on polyurethane prepolymers blended with latex modifiers in accordance with the above-mentioned Wood patent have been found to be useful in the practice of the invention. Such polyether polyurethane prepolymers are currently available from W.R. Grace Company under the HYPOL ® brand name. Suitable latex modifiers are available from Union Carbide Corporation under the UCAR ® brand name and from Rohm and Haas Company under the RHOPLEX ® brand name. In addition, I have found that viscoelastic foam compositions whose recovery times are temperature dependent can be produced from such latex modified polyurethane compositions. Also preferred materials for the nose and tail sections 3 and 5 are polyvinylchoride foam compositions, again, due to their formulation flexibility, easy processing characteristics and economics. Polyvinylchloride foam compositions generally have stronger cell walls and tend to be more amenable to reuse and washing.

The nose section 3 of the earplug of the invention has a recovery time of at least 1 second from 60 percent compression to 40% compression thereof. Unless otherwise stipulated herein, the recovery times mentioned herein are taken at about room temperature, meaning approximately 70°-72° F. (21°-23° C.). Where the polymeric foam composition employed for the nose section 3 is such that the recovery rate thereof is not markedly inversely temperature dependent, the maximum recovery time of said nose section 3 should not normally exceed 60 seconds and will preferably reside within a range of between 10 and 60 seconds. In a preferred embodiment of the invention, however, the polymeric foam composition employed for the nose section 3 is of a character such that the recovery time thereof is markedly and inversely temperature dependent. Where this condition is met, the 60-40 percent compression recovery time of the nose section 3 at room temperature (70°-72° F., 21°-23° C.) should be greater than 60 seconds and the recovery time at body temperature, body temperature meaning approximately 96° F. (35.6° C.), should be substantially less than the recovery time at room temperature and in any event, no greater than 90 seconds. By substantially less is meant that the recovery time at body temperature should be a small fraction, e.g. two-thirds or less, of the recovery time at room temperature. In other words, the nose section 3 should recover about 1½ times faster at body temperature than it does at room temperature. The nose section 3 of earplugs in accordance with this preferred embodiment of the invention generally need not be compressed greatly below the size of the ear canals into which they are to be inserted in order to assure adequate time in which to insert them and the user need not rush the insertion step in order to assure adequate depth of insertion thereof. In addition, where the room temperature recovery time of the nose section 3 is greater than about 60 seconds and the body temperature recovery time in minutes multiplied by the density (in pounds per cubic foot) squared is greater than about 40, it would appear that the exceptional dynamic stiffness exhibited by such temperature dependent viscoelastic polymeric foam materials results in improved attenuation of this preferred embodiment of the earplug hearing protector in the lower range of audible frequencies (ca. 125–1000 Hz). Indeed, as will be shown in Example 3 hereof, resilient polymeric foam earplugs consisting solely of a nose section 3 composed of such a polymeric foam material exhibit the aforementioned low frequency attenuation benefits.

Whatever the recovery time characteristics of the nose section 3, it is additionally important that the equilibrium pressure exerted by said nose section at 40% compression thereof, at room temperature, reside within the range of from 0.2 to 1.3 p.s.i. and preferably reside within the range of from 0.35 to 1.0 p.s.i. Adherence to these criteria assures that the inserted and partially recovered nose section 3 of the earplug will achieve and maintain comfortable acoustic occlusion of the ear canal during use.

With respect to the tail section 5 of the earplug construction of the invention it is important that the recovery time thereof from 60 percent compression to 40 percent compression thereof be substantially less than, i.e. shorter, that of nose section 3. By substantially less is meant that, the recovery time of the tail section 5 should be no greater than 50 percent of the recovery time of the nose section 3 and, in any event, should be no greater than 5 seconds. Preferably, the recovery time of said tail section 5 will be no greater than 2 seconds. It should be noted that many rapid recovery foam compositions meeting the above characteristics are well known to those skilled in the art and can be employed in the tail section 5.

The tail section 5 of the earplug construction of the invention is intended to remain outside the ear canal during use. Consequently, the pressure exerted by said tail section 5 at 40% compression thereof is not critical. Nevertheless, it is desirable that the stiffness of the tail section 5 be no greater than about that of the nose section 3 and, even more desirably, ill be substantially less as measured by either the Shore 00 or instant pressure methods, as described in greater detail further in the disclosure. By meeting either of these criteria, the rolldown step in utilizing the earplug construction of the invention can be facilitated.

In use the earplug construction of the invention is initially rolled down to below the size of the ear canal into which it is to be inserted, the tail section 5 thereof grasped between thumb and forefinger, and the slowly recovering nose section 3 thereof inserted into the ear canal to the full depth of said nose section, thereby establishing the tail section 5 outside the ear canal proper but within the concha. By virtue of the relatively rapid elastic recovery of the tail section 5, said tail section functions as a stop means to prevent overinsertion of the plug and, in many instances, will bear sufficiently upon the structure of the concha as to quickly and lightly secure the inserted nose section 3 of the earplug at a proper depth and position of insertion until such time as said relatively slow recovery viscoelastic nose section itself recovers to contact the enclosing ear canal wall and develop a stable acoustic seal therewith. Thus, in many instances the user of the earplug construction of the present invention will find substantial relief from the bother imposed by the prior art rolldown type polymeric foam earplugs wherein it is usually necessary to manually hold the inserted plug in position with a fingertip until seating of the inserted portion thereof occurs within the ear canal.

It will be understood, of course, that the recovery properties of that portion of the viscoelastic foam nose section 3 in the region of the parting line 7 will be affected to a greater or lesser degree by the proximity of the adjacent, relatively more elastic, tail section 5. Similarly, the recovery properties of that portion of the relatively elastic foam tail section 5 in the region of said parting line 7 will also be affected to at least some extent by the proximity of the adjacent more viscoelastic nose section 3.

The length of the nose section 3 is subject to considerable variation depending upon such parameters as the recovery properties of the particular viscoelastic polymeric foam composition selected therefore and the degree of hearing protection desired of the completed earplug construction. Generally speaking, it can be said that, for any given polymeric foam composition, the greater the contact area achieved between the nose section 3 and the ear canal wall the greater the hearing protection properties afforded the user. Therefore, for a nose section 3 of given diameter and given composition, the greater the length thereof (up to the maximum length of the average ear canal) the greater will be the hearing protection properties afforded by the completed earplug construction. However, there are many environmental noise situations in which adequate hearing protection can be provided by earplug constructions in which the length of the nose section 3 provides less than the optimum attenuation properties of which such earplug construction are capable. I have found, for instance, that earplugs having nose sections 3 of from about 0.25 inch to about 0.75 inch (6.35 mm to about 19.05 mm) are generally useful in the practice of the invention. Optimum attenuation for a large segment of the population is generally provided when the length of the nose section 3 is from 0.5 to 0.6 inch (12.7 mm to 15 mm), and as such, is preferred.

Since the relatively elastic tail section 5 of the earplug construction of the invention is intended to reside outside the ear canal proper, the length thereof is not generally critical provided that it be sufficient to be readily grasped between thumb and forefinger and to adequately serve its purpose as a stop means to limit the depth of insertion of the nose section 3 into the ear canal. I have found that these functions can generally be served when the length of the tail section 5 is at least 0.1 inch (2.54 mm) with lengths between 0.2 inch (5 mm) and 0.4 inch (10 mm) being especially well suited. Where the length of the tail section 5 is greater than about 0.4 inch (10 mm) it can extend outside the concha during use. A tail section 5 length sufficient to cause protrusion thereof outside the concha is unnecessary to serve the contemplated functions of the tail section 5 and can be obtrusive or bothersome to the user, particularly during use of the earplug construction of the invention as a sleep aid wherein contact between the protruding tail section 5 and a pillow is likely to occur.

In the working examples to follow, use is made of certain test apparatus and analytical protocols to derive the information reported therein. There follows a brief description of this apparatus and the protocols employed in testing specimen earplugs produced in accordance with the examples.

BRIEF DESCRIPTION OF TEST APPARATUS AND TEST PROTOCOLS EMPLOYED IN THE WORKING EXAMPLES

Test Apparatus

Figure 3:
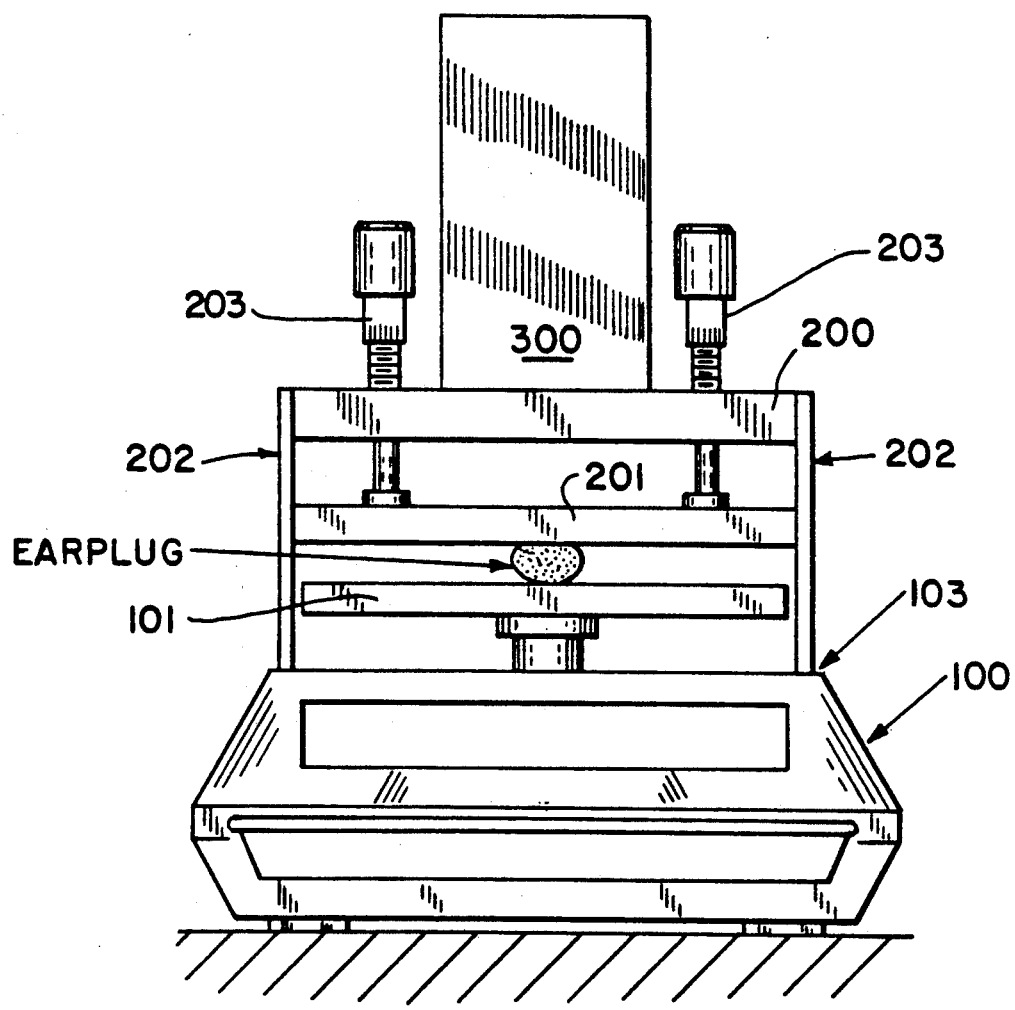
FIG. 3 is a front view of the testing apparatus utilized in the working examples hereof to determine recovery time, equilibrium pressure and other properties of the specimen earplugs prepared therein.

Referring to FIG. 3 hereof, the test apparatus employed for recovery time, equilibrium pressure and certain other tests comprises a self-taring electronic balance 100 whose balance pan is replace by a flat plate 101. A removable bridge 200 is supported at a fixed distance above the plate 101 by means of side supports 202. The bridge 200 and side plates 202 are sized such that the support for the bridge is established on the upper surface 103 of the balance 100. An adjustable flat upper plate 201 is suspended below the bridge 200 by means of a pair of axially adjustable vernier jackscrew support means 203 spaced equidistantly to either side of the center of the bridge 200. In order to provide removability of the bridge 200 from the balance the side supports 202 thereof are not affixed to the balance. Instead, stability of the removable mounting of the bridge 200 to the balance 100 and assurance of adequate weight to compress the plug specimens is provided by a relatively heavy mass 300 affixed to the top of the bridge 200, the total weight of this removable system being 12.3 lbs (5583 gm). Precise spacing of the adjustable upper plate 201 from the plate 101 of balance 100 is achieved by suitable adjustment of the vernier jackscrew support means 203.

Recovery Time Test

Specimen earplugs are die-stamped from polymeric foam sheets so as to produce cylinders having lengths generally within the range of from about 0.5 inch (12.7 mm) to about 0.9 inch (22.9 mm). For the room temperature test the apparatus described above is stationed in a laboratory environment and the temperature of the entire mass thereof allowed to equilibrate to the laboratory temperature. The upper plate 201 is adjusted to be parallel to and spaced from the plate 101 at a distance equivalent to 60% of the specimen earplug's diameter. An earplug specimen which has been stored for at least 24 hours at 50% relative humidity and at a temperature of from 21° C. to 23° C. is twirled lengthwise between the fingers for 20 seconds and with increasing force such that the earplug is reduced to a tight cylinder having a diameter of about 40% of its original diameter. The earplug is then inserted lengthwise and released between the parallel plates of the apparatus and the elapsed time between said release and the attainment of 75% line contact of the recovering plug with the plates measured with a stopwatch or other suitable timing device.

Where the recovery time test is accomplished at 96° F. (35.6° C.), the test apparatus is first stationed in a forced convection laboratory oven whose door has been replaced with a thick polymethylmethacrylate sheet having an access hatch through which wares may be introduced into the oven and manipulated therewithin. The set point oven temperature is 96° F. (35.6° C.) and, preparatory to carrying out specimen testing, the test apparatus heated therein for a period sufficient to allow the entire mass of the test apparatus to equilibrate to the set point temperature. Throughout the 96° F. recovery time and equilibrium pressure tests the test apparatus is maintained in the oven and, with the notable exception of the earplug specimen storage and roll down steps all other manipulations are made within the oven and all observations are made through the polymethylmethacrylate sheet.

In order to maximize the relative precision of the test, a number of specimen plugs of the same experimental batch may be taken and the results averaged. In testing the composite foam plugs of the invention the recovery time may be taken for the nose section alone or for the entire earplug. Alternatively, the nose and tail sections can first be separated, such as by careful cutting of the plug along the parting line between the respective sections, and the recovery times of the separated sections determined individually.

40% Compression Equilibrium Pressure Tests

The equilibrium pressure test is accomplished during the course of the above recovery time testing procedure. Once the recovery time has been determined, the plug specimen is allowed to remain between the parallel plates and the force reading of the balance monitored until it reaches a maximum and stabilizes. This force is taken as the equilibrium force and is converted to a force per unit area value. The contact area of the specimen earplug with the constraining plates is determined by measuring the area of the "footprint" of the earplug on the parallel plates. One method of attaining the area of this footprint is by utilizing a sooted glass plate attached to the adjustable upper plate 201. Using an optical comparator the smudge created on the sooted glass plate by the plug upon recovery to 60% of its original diameter is traced and the area thereof measured with a planimeter to obtain the total contact area. Where other specimen plugs of the same formulations and diameters, but of different lengths, are to be tested, the areas thereof can be calculated utilizing the original smudge area. In this, the width of the original smudge is calculated by dividing the area thereof by the original plug specimen's length. Then the contact areas of the subsequent plug specimens of different lengths can be calculated by multiplying this calculated width by the measured length of the particular plug specimen of different length subsequently tested and taking this result to be the area of contact of the specimen on each plate. I have found little error to be introduced in these calculations, provided that the difference in length between the original plug and the subsequent plug specimen is no greater than about 0.2 inch (5 mm). Herein, all equilibrium pressure values are reported in pounds per square inch (p.s.i.).

Instant Pressure Test

This parameter is defined as the instant force reading divided by the area of contact as measured during the course of the above equilibrium pressure test. In carrying out the instant pressure test the same plug specimen is utilized. The adjustable upper plate 201, bridge 200 and mass 300 are removed from the balance. The plug specimen residing on the lower plate 101 from the previous equilibrium pressure test is then allowed to recover fully to its original diameter. Then, the upper plate 201, still adjusted to 60% of the plug specimen's original diameter and the associated bridge 200 without mass 300 are replaced firmly, but without impact, onto the balance and the force exerted on the lower plate 101 immediately taken. Generally, the instant pressure reading can be used as a suitable measure of stiffness.

Shore 00 Durometer Test

Shore 00 Durometer hardness values of the specimen earplugs are determined by holding the Shore Durometer apparatus (available from the Shore Instrument Co., Jamaica, N.Y.) and specimen in each hand and manually applying the indentor foot of the durometer to the nose section of the specimen without impact, but with rapid steady contact therewith. Readings were taken immediately upon application of the indentor foot to the specimen and 15 seconds thereafter and are reported in that order herein. Where the Shore 00 Durometer values for tail sections of the earplug specimen were taken, a number of tail sections were first carefully cut from the nose sections of several specimen earplugs. The collected tail sections were then stacked one upon the other in order to provide an overall tail section specimen thickness of about ½ inch (12.7 mm). The indentor foot of the durometer was then applied to this stack in the manner previously indicated. As with the instant pressure test, the Shore 00 Durometer reading can also be used as a suitable measure of stiffness.

Apparent Density Test

Overall earplug specimen apparent density is determined by weighing the specimen and dividing the weight by the specimen volume as calculated from the dimensions thereof. The dimensions are determined by a contactless method utilizing light since contact methods of measuring the specimens tend to result in at least some compression of the material and can lead to inexact measurements. For instance, a backlighted thickness gauge can be used, contact of the specimen with said gauge being determined visually. An optical comparator may also be utilized for the dimensional measurements. The apparent densities of the respective nose and tail sections of the earplug specimens are determined by separating the nose and tail sections along the parting lines and carrying out the weighing, measuring and volume calculations for the separated sections in the manner outlined above.

A number of non-limiting examples of the present invention follows.

EXAMPLE 1

In this example polyvinylchloride foam earplugs in accordance with the invention and appearing as in FIG. 1 hereof are prepared by first preparing a two-layer free-blown, i.e. not in a molding press or the like, polyvinylchloride composite foam sheet followed by die cutting of cylindrical earplug specimens therefrom.

Figure 4:
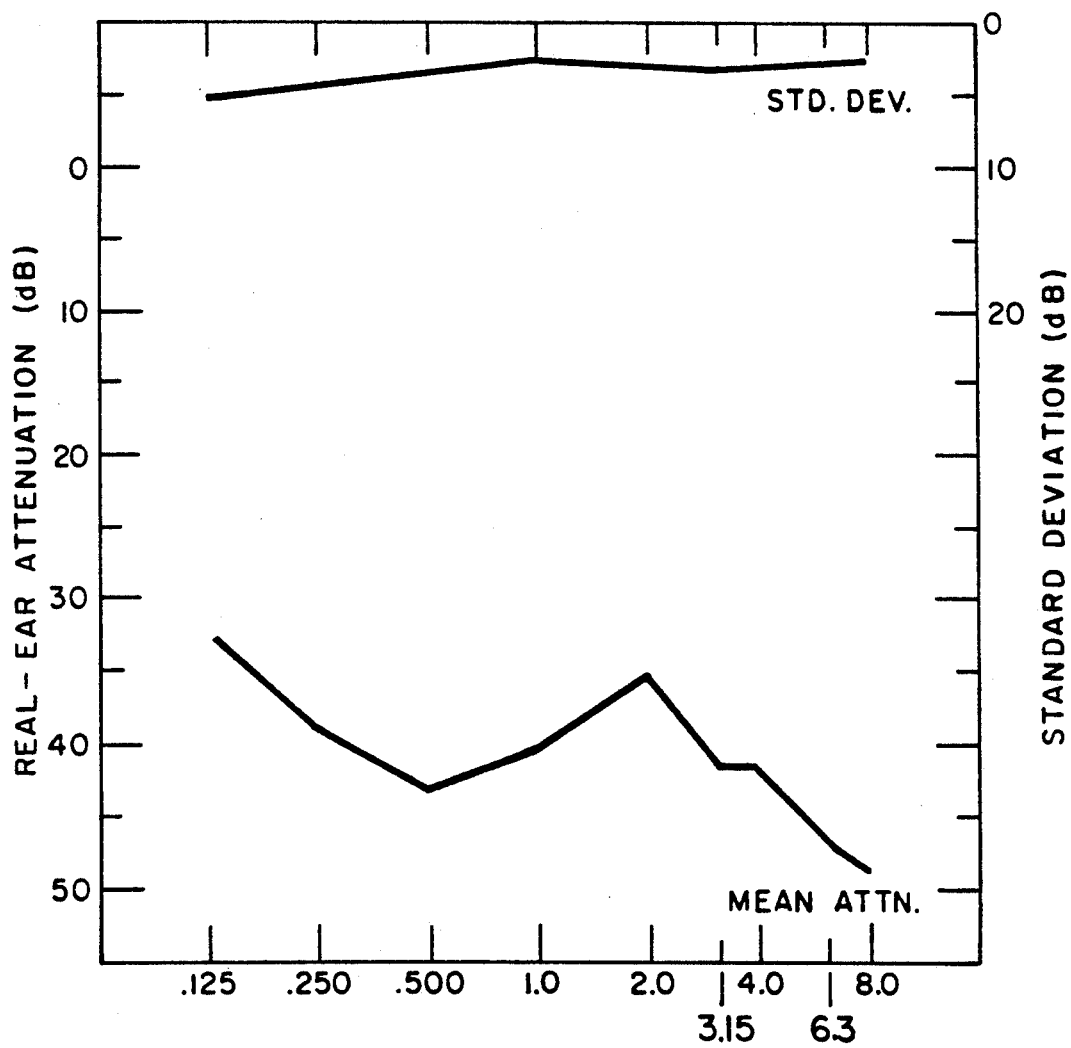
FIG. 4 is a plot of attenuation as a function of frequency of an exemplary earplug in accordance with the invention.

The two-layer polyvinylchloride foam sheet is prepared as follows. Onto a release paper held flat by means of a vacuum plate there is deposited a yellow polyvinylchloride plastisol formulation formulated to result in a relatively fast recovery, elastic foam layer. This plastisol formulation is drawn down with a Gardner knife held at a 0.025 inch (0.635 mm) spacing from the surface of the release paper. The release paper, containing the plastisol drawdown thereon, is then placed into an oven preheated to 415° F. (213° C.) for a period of 20 seconds in order to gel the plastisol drawdown. The release paper is then returned to the vacuum plate and, after cooling, a strip of about 0.25 inch (6.35 mm) width is cut away from each side of the gelled drawdown, the cutting being accomplished with due care so as to avoid injury to the underlying surface of the release paper. Next, a white polyvinylchloride plastisol formulation formulated to produce a relatively slow recovery, viscoelastic foam layer, is deposited onto the gelled yellow plastisol drawdown and drawn down at a Gardner knife setting of 0.086 inch (2.18 mm) such that the knife is supported on the release paper and does not contact the underlying yellow gelled plastisol drawdown. The release paper is then removed from the vacuum plate and returned to the 415° F. (213° C.) oven for a period of 6.5 minutes in order to fuse and blow the superposed plastisol formulations. The resulting two-layer polyvinylchloride foam sheet is removed from the oven and cooled to room temperature. Next, earplug specimens are die-stamped from the two-layer foam sheet using dies which produce cylindrical earplug specimens having nominal diameters of 0.535 inch (13.59 mm). The specimen plugs are then stored for at least 24 hours at a temperature of between 70° F. and 72° F. (21° C. and 23° C.) and at 50% relative humidity preceding testing thereof in accordance with the protocols set forth hereinabove. The specific plastisol formulations employed and the results of physical testing of the earplug specimens are shown in Table I, following. In addition, attenuation tests of a production lot (Lot K037A) of similar earplug specimens produced from a two-layer foam prepared on a production blowing line and utilizing similar plastisol formulations were carried out in accordance with the test protocol of ANSI S12.6-1984. The resulting attenuation plot is shown in FIG. 4 hereof. The subjects generally found said tail section 5 to function effectively as a stop means and to effectively limit the depth of insertion of the nose section 3 of the earplug into the ear canal.

TABLE I

POLYVINYLCHLORIDE PLASTISOL FORMULATIONS

| Ingredient | Parts by Weight | |
|---|---|---|
| | Nose Section 3 | Tail Section 5 |
| Tenneco 1732 PVC Resin[1] | 115 | 115 |
| Admex 523[2] | 95 | 50 |
| Paraplex ® G23[3] | 5 | 5 |
| Antimony Oxide[4] | 8 | 8 |
| Vanstay ® 8014[5] | 3 | 3 |
| Stanclere 876[6] | 2 | 2 |
| VS103[7] | 1 | 1 |
| Celogen ® 150[8] | 8 | 8 |
| Dioctyl azelate[9] | — | 45 |
| Cab-O-Sil ® M5[10] | — | 1 |
| Stanton 12PCO1[11] | — | 1 |

[1]A plastisol grade polyvinylcholoride homopolymer manufactured by Occidental Petroleum Company. PVC Resins and Compounds Division. Pottstown. PA.
[2]An aromatic polyester plasticizer produced by HULS America. Inc. Box 88700, Chicago. IL.
[3]Plasticizer/Stabilizer. C. P. Hall. 7300 S. Central Ave., Chicago. IL.
[4]Antimony Oxide. Flame retardant, ANZON, Inc.. Box 8068-207, Philadelphia. PA.
[5]A stabilizer produced by R. T. Vanderbilt Co., Inc., New York. New York.
[6]Stabilizer. AKZO. Inc. Box 93858, Chicago. IL.
[7]Foam Stabilizer. Air Products Co., Allentown, PA.
[8]Blowing Agent. Uniroyal Chemical Co.. Nangatuck. CT.
[9]Dioctyl azelate. plasticizer, Emery Industries. Cincinnati. OH.
[10]A pyrogenic silica. Cabot Corporation. Cab-O-Sil Division, Tuscola, Illinois.
[11]Colorant. Harwick Chemical Co., Elkgrove. IL, Offices Akron. OH.

| PHYSICAL PROPERTIES OF EARPLUG SPECIMENS | |
|---|---|
| Weight (gm) | .3037 |
| Total length (in) | .825 |
| Length nose section 3 (in) | .62 |
| Length tail section 5 (in) | .205 |
| Diameter (in) | .535 |
| Overall apparent density (lbs/ft³) | 6.24 |
| Nose 3 apparent density (lbs/ft³) | 6.30 |
| Tail 5 apparent density (lbs/ft³) | 6.05 |
| Overall 60–40% compression recovery time (sec) | 6.88 |
| Overall exerted force at equilibrium (gms) | 74.77 |
| Contact width at equilibrium (in) | .32 |
| Overall equilibrium pressure at 40% compression (p.s.i.) | .62 |
| Nose 3 exerted force at equilibrium (gms) | 60.47 |
| Nose 3 equilibrium pressure at 40% compression (p.s.i.) | .67 |
| 60–40% recovery time of tail section 5 (sec) | 1.68 |
| Shore 00 Durometer nose section 3 (instant/15 secs) | 43/33 |
| Shore 00 Durometer tail section 5 (instant/15 secs) | 20/19 |
| Instant pressure of nose section 3 (p.s.i.) | 3.99 |
| Instant pressure of tail section 5 (p.s.i.) | 1.83 |

EXAMPLE 2

Earplug specimens in accordance with the invention were die-stamped from two-layer composite sheets of acrylic latex modified polyetherpolyurethane foams. The composite foam sheets were prepared as follows.

The polyetherpolyurethane prepolymer formulation adapted to provide the relatively elastic and short recovery time foam layer for tail section 5 is placed onto a release paper held flat by a vacuum plate and drawn down with a polypropylene knife having an 0.2 inch deep blade. The prepolymer formulation is prepared by mixing of the ingredients in a variable high speed mixer set at as high a speed as possible without creating a vortex. The mixed formulation is then deposited onto the release paper and doctor bladed with the knife held at a sufficiently acute angle as to provide a resultant foam of the desired thickness. Upon completion of the draw down, a second sheet of release paper is placed onto tee top of the draw down and the system allowed to cure at ambient laboratory conditions.

Next, the polyetherpolyurethane prepolymer formulation adapted to provide the relatively viscoelastic and long recovery time foam layer is prepared, deposited onto a separate sheet of release paper and drawn down in the manner described above, but at a somewhat steeper knife angle, the spacing of the blade from the paper being sufficient to produce a foam of the desired thickness. The cover sheet release paper is removed from the already cured first draw down and said first draw down is laid, exposed face down, onto the fresh second draw down. The resulting two-layer composite system is then allowed to cure at ambient laboratory conditions, the release paper sheets removed from both sides thereof and the composite foam sheet material dried for two hours at 50° C. Specimen plugs of 0.535 nominal diameter are die-stamped from the cured and dried composite sheet material, the plugs dried for ½ hour at 50° C. and then stored at room temperature and 50% relative humidity for at least 1 month prior to final testing thereof. This is done to ensure completeness of cure and crystallite formation. The prepolymer formulations employed and the physical test results for these specimen earplugs are set forth in Table 2, which follows. As will be noted therefrom the recover times of the nose sections 3 of the specimen earplugs, D/E and Z/E, are markedly inversely temperature dependent, each having a room temperature recover time of greater than one minute and having a recovery time and at 96° F. (35.6° C.) of only a small fraction of the room temperature recovery time of less than 90 seconds. While quantitative attenuation tests on human subjects were not accomplished using these earplug specimens, qualitative tests indicated that the attenuation performance thereof was effective for many environmental noise conditions and that insertion of the rolled down nose sections 3 of the plugs into the ear canals to the proper depth was facilitated by the combination of the presence of the relatively elastic tail sections 5 and the temperature sensitive recovery times of the viscoelastic nose sections 3.

During the recovery time testing of earplug specimens, it was observed that the leading end regions, i.e. the end inserted first into the ear canal, of the nose sections 3 thereof recovered somewhat more quickly than the remainder of the nose sections. This feature of the specimens, however, was determined to be useful and desirable since it provided at least some early attenuation soon after insertion into the ear canal and served to coaxially position the nose section 3 in the ear canal during the major portion of its recovery therewithin. Several of the nose sections 3 of the Z/E specimens were longitudinally sectioned and apparent densities determined for each section. It was noted that an apparent density gradient existed across the thickness of the viscoelastic foam sheet employed for these nose sections 3, the apparent densities in the regions of the surface of said foam sheet being substantially greater than the apparent density in the central or core region thereof. It is believed that the principal cause of the 96° F. tip recovery phenomenon noted above was due to this apparent density gradient and it is further believed that the gradient was established during blowing of the prepolymer formulation in the free atmosphere whereby the exotherm of the reaction was better insulated in the core of the sheet, thereby establishing a higher blowing temperature in the core of the sheet than existed in the surface regions thereof.

TABLE 2

POLYETHERPOLYURETHANE PREPOLYMER FORMULATIONS

| Ingredient | Parts by Weight | | | |
|---|---|---|---|---|
| | Nose Section 3 | | | Tail Section 5 |
| Formulation Identification | D | F | Z | E |
| HYPOL ® 3000[1] | 75 | 30 | 150 | — |
| HYPOL ® 2002[2] | 75 | 120 | — | 150 |
| UCAR ® 154[3] | 80 | 120 | 150 | — |
| BRIJ ® 72[4] (20% Aq. Sol.) | — | — | — | 15 |
| H₂O Water | 20 | 30 | — | 108 |
| Sunsperse Orange OHD 6014[5] | — | — | — | 1 |

[1]Polyetherpolyurethane prepolymer, W. R. Grace Company, Lexington, MA.
[2]Polyetherpolyurethane prepolymer, W. R. Grace Company, Lexington, MA.
[3]Self cross-linking acrylic resin latex, Union Carbide Corporation, Cary, NC.
[4]Surfactant, ICI Americas Inc., Wilmington, Delaware.
[5]Colorant, Sun Chemical Corp., Cincinnati, OH.

TABLE 3

PHYSICAL PROPERTIES OF EARPLUG SPECIMENS

| | Nose Section 3 | | |
|---|---|---|---|
| | D | F | Z |
| | Tail Section 5 | | |
| Formulation Identification | E | E | E |
| Nose Length (in.) | .519 | .587 | .714 |
| Tail Length (in.) | .250 | .165 | .180 |
| Diameter (in.) | .547 | .546 | .518 |
| Weight Total (gms.) | .361 | .353 | .292 |
| Nose Density (lbs/ft³) | 7.99 | 8.27 | 5.68 |
| Tail Density (lbs/ft³) | 7.79 | 7.79 | 7.79 |
| Nose Recovery Time, 72° F. (sec.)** | 78.2 | 31.9 | 277 |
| Nose First Touches, 72° F. (sec.)** | 20.5 | 9.0 | 106 |
| Nose Equilibrium Pressure, 72° F. (p.s.i.)** | 0.74 | 0.76 | 0.29 |
| Nose Instant Pressure, 72° F. (p.s.i.)** | 1.90 | 1.62 | 0.97 |
| Tail Instant Pressure, 72° F. (p.s.i.)** | 1.10 | 1.29 | 1.19 |
| Recovery Time, 72° F. (sec.)** | Inst. | Inst. | Inst. |
| Nose Recovery Time, 96° F. (sec.)** | 30.4 | 25.3 | 57.4 |
| Nose First Touches, 96° F. (sec.)** | 20.4 | 17.0 | 37.7 |
| Nose Equilibrium Pressure, 96° F. (p.s.i.)** | 0.79 | 0.80 | 0.30 |
| Tail Recovery Time, 96° F. (sec.)** | Inst. | Inst. | Inst. |
| 70° F. Nose Approx. Time to Equilibrium (min.)** | 27 | 10 | 45 |
| 96° F. Nose Approx. Time to Equilibrium (min.)** | 3 | 2 | 10 |
| Nose, Shore 00 Durometer (Instant/15 sec.)** | 27/24 | 23/20 | 27/21 |
| Tail Shore 00 Durometer (Instant/15 sec.)** | 21/21 | 21/21 | 21/21 |

**Determination made by cutting identified sections from specimens. Measurement was of individual specimens. Equilibrium pressure was measured by inserting compressed section into the test apparatus, measuring force and calculating the equilibrium pressure by dividing this force by the contact area of the specimen with the constraining plate 201 of FIG. 3 apparatus.

EXAMPLE 3

Figure 5:
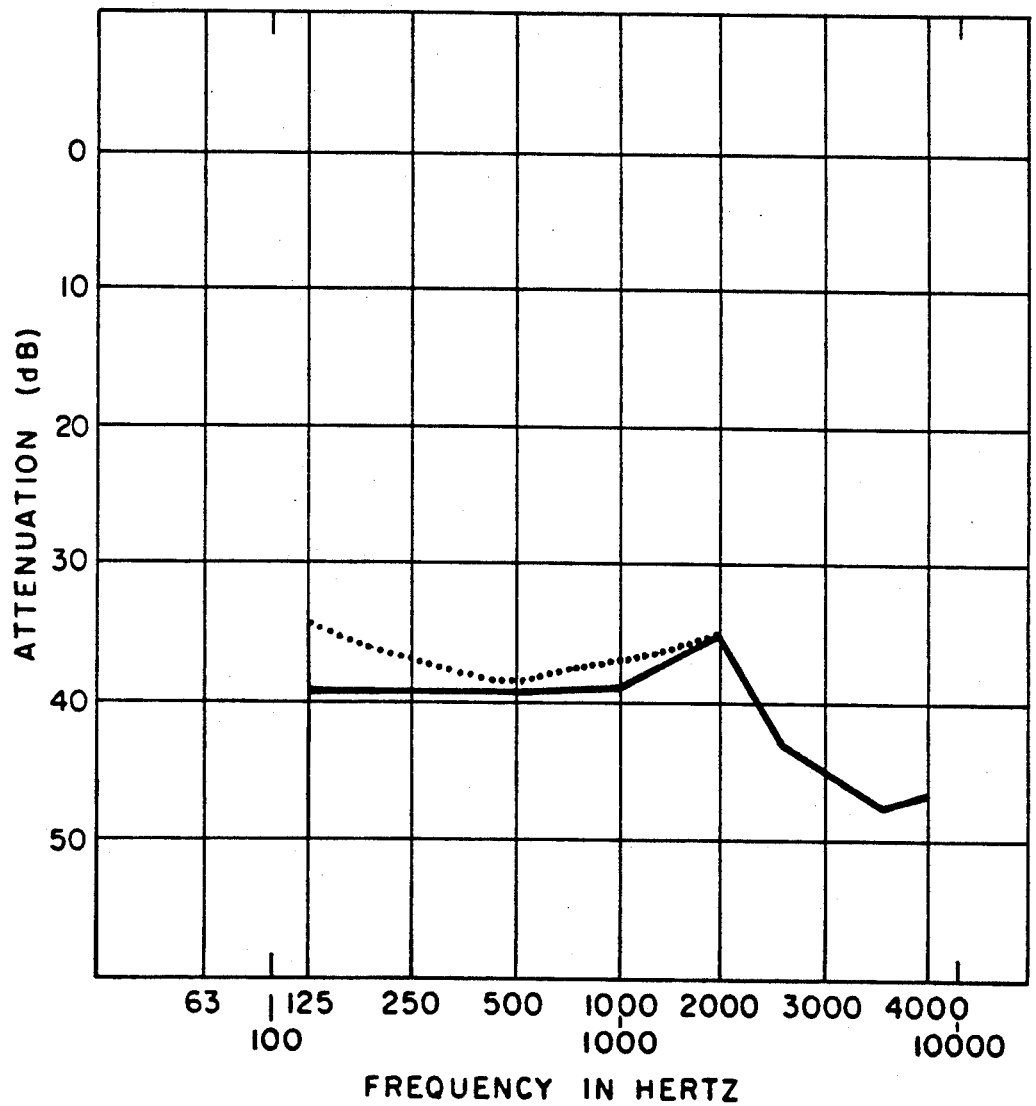
FIG. 5 is a plot of attenuation as a function of frequency of an exemplary earplug in accordance with a preferred embodiment of the invention and, for comparison purposes, of a commercially available polymeric foam earplug of the roll-down type as disclosed in U.S. Pat. No. Re. 29,487.

In this example, earplug specimens are prepared consisting solely of a nose section 3 composed of an acrylic latex modified polyetherpolyurethane foam whose recovery time property is markedly inversely temperature dependent. The prepolymer formulation is prepared, placed onto release paper, doctor bladed and cured in the general manner outlined for the relatively rapid recovery elastic foam layer preparation in Example 2. The polyetherpolyurethane formulation employed in the present example was a simple two-component mixture consisting of 150 parts by weight of Hypol ® 3000 polyetherpolyurethane prepolymer and 225 parts by weight of UCAR ® 154 acrylic latex. After drawing down and curing at ambient conditions, the resulting foam sheet was dried, die cut into earplug specimens, and the specimens re-dried and stored several months at laboratory temperature and 50% relative humidity prior to testing, as in Example 2. The physical properties of the specimen earplugs of the instant example are reported in Table 3, below. Modified ANSI S12.6-84 attenuation testing thereof was performed as in Example 1 and the results thereof are plotted in FIG. 5 as a solid line. For purposes of comparison attenuation test results of presently available commercial slow recovery foam roll-down type earplugs, E-A-R ® Foam Earplugs, E-A-R Division, Cabot Safety Corporation, Indianapolis, Ind., as determined for the same subjects at the same time, are also plotted in dotted line form. As can be noted from FIG. 5, the experimental plugs of this example display improved low frequency attenuation characteristics over this state-of-the-art commercial earplug. During the 96° F. recovery time testing of the earplug specimens it was noted that the ends thereof recovered somewhat more rapidly than did the centeral regions. The specimens, during the early stages of their recovery from 60% compression, assumed a distinctly toroidal, rather than cylindrical, profile. Upon longitudinal sectioning and measurement of apparent density of the sections thereof the density gradient feature spoken of with respect to the Z/E specimens of Example 2 was again noted. More specifically, the density of the foam was found to be substantially greater in the end regions of the specimens as compared to that of the central region intermediate ends. As illustrated in Table 3 below, this density gradient caused the tip of the Nose Section 3 to make contact with the ear canal, i.e. at 96° F., in 13.3 seconds, or approximately 1/5th of the recovery time at room temperature.

TABLE 3

PHYSICAL PROPERTIES OF EARPLUG SPECIMENS

| | |
|---|---|
| Weight (gms) | 0.4050 |
| Length (inches) | 0.741 |
| Diameter (inches) | 0.532 |
| Apparent Density (lbs/ft³) | 9.39 |
| Recovery Time at 70–72° F. (sec.) | 77.3 |
| Recovery Time at 96° F. (sec.) | 37.2 |
| Nose first touches 96° F. (sec.) | 13.3 |
| Equilibrium Pressure (p.s.i.) | 0.69 |

TABLE 3-continued

PHYSICAL PROPERTIES OF EARPLUG SPECIMENS

| Shore 00 Durometer (instant/15 sec.) | 33/29 |

While I have described and shown above certain preferred embodiments of the invention, it is to be distinctly understood that the invention is not limited thereto, but may be variously modified to produce other embodiments and equivalent modifications thereof without departing from its essential scope and spirit. For instance, the earplug constructions of the present invention can be employed effectively as ear stopples in an earphone device wherein an earplug such as described hereinbefore is modified by providing it with an axial bore therethough, which bore is adapted to receive a sound conducting tube or miniature speaker therein. Moreover, while the exemplary earplug constructions hereof where produced by die cutting from two-layer composite sheets prepared by free blowing of polymeric foam precursor formulations to the atmosphere, it should be understood that the invention can also be realized by molding of suitable precursor polymeric foam compositions. The use of molding techniques can be beneficial when earplug constructions of complex shapes, such as shown in FIG. 2, are desired. It should be understood, of course, that precursor polymeric foam formulations utilized for free blowing of foam sheets of specified recovery properties will not normally produce molded foam wares having equivalent recovery properties. For a given foam precursor formulation in-mold foaming, particularly closed mold foaming, tends to produce denser, more homogenous foam wares than does a free blowing technique. Thus, where molding of an earplug construction in accordance with the invention is entertained, adjustment of the precursor formulations specifically described in the working examples hereof may be necessary in order to realize the recovery properties required of the invention. Such formulation adjustment and the selection of appropriate molding parameters reside within the skill of the art.

The true scope of the invention is now particularly pointed out in the appended claims.

I claim:

1. A roll-down type earplug construction comprising a resilient polymeric foam body the cellular volume of said foam body being gas-filled, said body comprising a nose section and, coextensive therewith, a tail section, said nose section being composed of a slow recovery, viscoelastic, polymeric foam and being of a size and shape adapted to be compressed, inserted into the human ear canal and there allowed to expand and obturate the ear canal, said nose section having a room temperature recovery time from 60 percent compression to 40 percent compression thereof at least 1 second and an equilibrium pressure at 40 percent compression thereof of from 0.2 to 1.3 p.s.i., said tail section being composed of a relatively faster recover, more elastic, polymeric foam than that of said nose section, said tail section having a room temperature recovery time from 60 percent compression to 40 percent compression thereof of no greater than 50 percent of the recovery time of said nose section and no greater than 5 seconds.

2. The earplug construction of claim 1 wherein the recovery time of said nose section is relatively temperature insensitive and wherein the recovery time thereof at room temperature is between 1 and 60 seconds.

3. The earplug construction of claim 2 wherein the recovery time of said nose section at room temperature is between 10 and 60 seconds.

4. The earplug construction of claim 1 wherein the recovery time of said nose section is markedly and inversely temperature dependent and wherein said recovery time at room temperature is greater than 60 seconds, wherein said recovery time at body temperature is no greater than 90 seconds and wherein said recovery time at body temperature is substantially less than said recovery time at room temperature.

5. The earplug construction of claim 4 wherein the recovery time of said nose section at body temperature is no greater than 60 seconds.

6. The earplug construction of claim 4 wherein at body temperature the leading end regions of said nose section recover substantially more quickly than the mid-length region thereof.

7. The earplug construction of claim 1 wherein the room temperature equilibrium pressure of said nose section at 40% compression thereof resides within the range of 0.35 and 1.0 p.s.i.

8. The earplug construction of claim 1 wherein the room temperature stiffness of said tail section is less than that of said nose section, as determined by the Shore 00 Durometer test.

9. The earplug construction of claim 1 wherein the room temperature stiffness of said tail section is less than that of said nose section, as determined by the instant pressure test.

10. The earplug construction of claim 1 wherein the room temperature recovery time of said tail section is no greater than 2 seconds.

11. The earplug construction of claim 1 wherein the length of said nose section resides within the range of 0.25 and 0.75 inch.

12. The earplug construction of claim 11 wherein the length of said nose section resides within the range of 0.5 and 0.6 inch.

13. The earplug construction of claim 1 wherein said nose section is composed of polyvinylchloride foam compositions.

14. The earplug construction of claim 1 wherein said nose section is composed of polyurethane foam compositions.

15. The earplug construction of claim 1 wherein said nose section is composed of polyetherpolyurethane foam compositions.

16. The earplug construction of claim 15 wherein said nose section is composed of latex modified polyetherpolyurethane foam compositions.

17. The earplug construction of claim 1 wherein said tail section is composed of polyvinylchloride foam compositions.

18. The earplug construction of claim 1 wherein said tail section is composed of polyurethane foam compositions.

19. The earplug construction of claim 1 wherein said tail section is composed of polyetherpolyurethane foam compositions.

20. The earplug construction of claim 15 wherein said tail section is composed of latex modified polyetherpolyurethane foam compositions.

21. The earplug construction of claim 6 wherein the end regions of said nose section are of greater apparent density than the mid-length region thereof.

22. The earplug construction of claim 1 wherein the length of said tail section is greater than 0.1 inch.

23. The earplug construction of claim 18 wherein the length of said tail section resides within the range of about 0.2 and about 0.4 inch.

* * * * *